United States Patent [19]

McGhee

[11] Patent Number: 5,349,081

[45] Date of Patent: Sep. 20, 1994

[54] PROCESS FOR PREPARING ISOCYANATES

[75] Inventor: William D. McGhee, Bridgeton, Mo.

[73] Assignee: Monsanto Company, St. Louis, Mo.

[21] Appl. No.: 6,409

[22] Filed: Jan. 21, 1993

[51] Int. Cl.$^5$ ............................................. C07C 263/04
[52] U.S. Cl. ..................................... 560/345; 560/338
[58] Field of Search ................................. 560/345, 338

[56] References Cited

U.S. PATENT DOCUMENTS

| | | | |
|---|---|---|---|
| 3,481,967 | 12/1969 | Ottmann et al. | 560/341 |
| 4,022,791 | 5/1977 | Welch, Jr. | 260/293.62 |
| 4,130,576 | 12/1978 | Hedaya et al. | 560/338 |
| 4,178,309 | 12/1979 | Luetzow et al. | 564/61 |
| 4,192,815 | 3/1980 | Sheludyakov et al. | 560/338 |
| 4,297,501 | 10/1981 | Becker et al. | 560/24 |
| 4,341,898 | 7/1982 | Milligan et al. | 560/24 |
| 4,388,238 | 6/1983 | Heitkämper et al. | 544/164 |
| 4,567,294 | 1/1986 | Dressel et al. | 562/555 |
| 4,582,923 | 4/1986 | Stammann et al. | 560/24 |
| 5,189,205 | 2/1993 | McGhee et al. | 560/345 |

OTHER PUBLICATIONS

Belforte, A., et al., "Incorporation and Deoxygenation of Carbon Dioxide: A Metal–Assisted Facile Conversion of Carbon dioxide and Primary Amines to Isocyanates", *Chem. Ber.*, 121, 1891–1897 (1988).

Hori, Y. et al., "New Organic Synthesis with DBU: Part 7, Synthesis of Carbonates and Carbamates with Carbon Dioxide Gas as the Starting Material", *Chemistry Express*, vol. 1, No. 4, pp. 224–227 (1986).

Schwesinger, R. and Schlemper, H., "Peralkylated Polyaminophasphazenes–Extremely Strong, Neutral Nitrogen Bases", *Agnew. Chem. Inc. Ed. Engl.*, 26, 11 (1987).

Schwesinger, R., "Extremely Strong, Non–ionic Bases: Synthesis and Application", *Chimia*, 29, 9 (1985).

*Primary Examiner*—José G. Dees
*Assistant Examiner*—Samuel Barts
*Attorney, Agent, or Firm*—Kenneth D. Goetz; Paul L. Passley; James C. Bolding

[57] ABSTRACT

A process for preparing isocyanates comprising (a) contacting carbon dioxide and a primary amine in the presence of an aprotic organic solvent and a base selected from the group consisting of a phosphazene compound, an organic, nitrogenous base and mixtures thereof, wherein the organic, nitrogenous base selected from the group consisting of guanidine compounds, amidine compounds, tertiary amines, pyridine and mixtures thereof to produce the corresponding ammonium carbamate salt, and (b) reacting the ammonium carbamate salt with an electrophilic or oxophilic dehydrating agent to produce the corresponding isocyanate. A second embodiment comprises recovering the ammonium carbamate salt of step (a) prior to reacting the ammonium carbamate salt with an electrophilic or oxophilic dehydrating agent in the presence of an aprotic organic solvent and a base selected from the group consisting of a phosphazene compound, an organic, nitrogenous base and mixtures thereof, wherein the organic, nitrogenous base selected from the group consisting of guanidine compounds, amidine compounds, tertiary amines, pyridine and mixtures thereof.

24 Claims, No Drawings

PROCESS FOR PREPARING ISOCYANATES

BACKGROUND OF THE INVENTION

The invention relates to a process for preparing isocyanates. In one aspect, the invention relates to a new and useful process for preparing isocyanates from primary amines, carbon dioxide and an electrophilic or oxophilic dehydrating agent.

Isocyanates, especially diisocyanates, are important commodity chemicals for use in applications such as preparation of urethane foam, urethane elastomers, coatings, insecticides, herbicides, and the like.

Commercially, the phosgenation of primary amines is by far the most widely used method for producing isocyanates. The use of phosgene, however, has several disadvantages. The phosgenation route is long, energy intensive and requires handling highly corrosive materials, e.g. hydrogen chloride, chlorine, sulfuric acid and nitric acid, and highly toxic reagents and intermediates, e.g. phosgene and chlorine. Furthermore, the phosgenation route requires use of process equipment which can withstand high temperatures and highly corrosive conditions resulting in increased capital costs.

One non-phosgene method for the preparation of isocyanates involves reaction of primary amines and $CO_2$ with a cobalt or manganese compound to produce metal carbamate complexes followed by reaction with an acyl halide in the presence of a solvent as is disclosed by A Belforte et al., "Incorporation and Deoxygenation of Carbon Dioxide: A Metal-assisted Facile Conversion of Carbon Dioxide and Primary Amines To Isocyanates" Chem. Ber., 121, 1891–1897(1988). However, the process described therein requires long reaction times and gives unsatisfactory yield of isocyanate for a commercially viable process.

Another non-phosgene route to isocyanates is found in U.S. Pat. No. 4,192,815 (Sheludyakov et al.) which discloses preparation of isocyanates by reacting a primary amine with $CO_2$ and hexamethyldisilazane in the presence of an acidic catalyst, e.g. $H_2SO_4$, followed by decomposition of the resulting silyl esters of carbamic acid in the presence of a dehydration agent. However, the process described therein requires long reaction times and is not commercially practicable.

A non-phosgene process for preparing isocyanates which is economical, commercially viable, and can produce isocyanates with high yield under mild reaction conditions and short reaction times is highly desirable.

SUMMARY OF THE INVENTION

It is an object of the invention to provide a process for preparing isocyanates. It is a further object of the invention to provide an efficient and economic process for preparing isocyanates that is commercially viable. It is a still further object of the invention to provide a process for preparing isocyanates which are not easily synthesized via phosgene routes.

According to the invention, a process for preparing isocyanates is provided which comprises (a) contacting carbon dioxide and a primary amine in the presence of an aprotic organic solvent and a base selected from the group consisting of a phosphazene compound, an organic, nitrogenous base and mixtures thereof, wherein the organic, nitrogenous base is selected from the group consisting of guanidine compounds, amidine compounds, tertiary amines, pyridine and mixtures thereof, under conditions of time and temperature sufficient to produce the corresponding ammonium carbamate salt, and (b) reacting the ammonium carbamate salt with an electrophilic or oxophilic dehydrating agent under reaction conditions of time and temperature sufficient to produce the corresponding isocyanate. In one embodiment, the ammonium carbamate salt of step (a) is recovered prior to reacting the ammonium carbamate salt with an electrophilic or oxophilic dehydrating agent in the presence of an aprotic organic solvent and a base selected from the group consisting of a phosphazene compound, an organic, nitrogenous base and mixtures thereof, wherein the organic, nitrogenous base is selected from the group consisting of guanidine compounds, amidine compounds, tertiary amines, pyridine and mixtures thereof.

DETAILED DESCRIPTION OF THE INVENTION

A first embodiment of the invention relates to a process for preparing isocyanates comprising (a) contacting $CO_2$ and a primary amine in the presence of an aprotic organic solvent and a base selected from the group consisting of a phosphazene compound, an organic, nitrogenous base and mixtures thereof, wherein the organic, nitrogenous base is selected from the group consisting of guanidine compounds, amidine compounds, tertiary amines, pyridine and mixtures thereof, under reaction conditions of time and temperature sufficient to produce the corresponding ammonium carbamate salt, and (b) reacting the ammonium carbamate salt with an electrophilic or oxophilic dehydrating agent under reaction conditions of time and temperature sufficient to produce the corresponding isocyanate.

A second embodiment of the invention relates to a process for preparing isocyanates comprising (a) contacting $CO_2$ and a primary amine in the presence of an aprotic organic solvent and a base selected from the group consisting of a phosphazene compound, an organic, nitrogenous base and mixtures thereof, wherein the organic, nitrogenous base is selected from the group consisting of guanidine compounds, amidine compounds, tertiary amines, pyridine and mixtures thereof, under reaction conditions of time and temperature sufficient to produce the corresponding ammonium carbamate salt, (b) recovering the ammonium carbamate salt, and (c) reacting the ammonium carbamate salt with an electrophilic or oxophilic dehydrating agent in the presence of an aprotic organic solvent and a base selected from the group consisting of a phosphazene compound, an organic, nitrogenous base and mixtures thereof, under reaction conditions of time and temperature sufficient to produce the corresponding isocyanate.

The isocyanates made according to this invention are readily recoverable and well suited for use in preparation of urethane foams, elastomers and coatings, insecticides, and herbicides.

The isocyanates produced by the process of the invention can be represented by the formula:

$$R_2-N=C=O$$

wherein $R_2$ is selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, a radical represented by the formula:

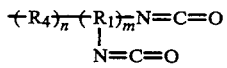

a radical represented by the formula:

a radical represented by the formula:

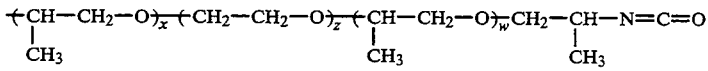

or isocyanates produced by the process of the invention can be represented by the formula:

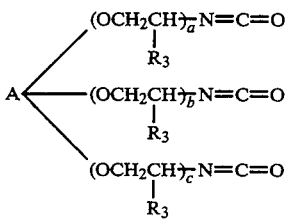

wherein $R_1$ and $R_4$ are independently selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, $x+w$ represents an integer from about 2 to about 70, z represents an integer from 0 to about 90, $x+w+z$ represents an integer from about 2 to about 100, a, b and c independently represent an integer from about 2 to about 30, and A represents a trihydric alcohol initiator such as glycerine or trimethylolpropane. In addition, $R_2$ may contain nonnucleophilic functional groups which do not react preferentially with the electrophilic or oxophilic dehydrating agent. Examples of suitable functional groups include esters, amides, urethanes, carbonates, and the like, and salts thereof.

Examples of isocyanates produced by the process of the invention include, but are not limited to, cyclohexyl isocyanate, octyl isocyanate, 1,4-cyclohexyl di-isocyanate, phenyl isocyanate, phenylalanine methyl ester isocyanate, glycine benzyl ester isocyanate, alanine benzyl ester isocyanate, phenylalanine ethyl ester isocyanate, leucine ethyl ester isocyanate, valine ethyl ester isocyanate, β-alanine ethyl ester isocyanate, glutamic acid diethyl ester isocyanate, hydrogenated toluene diisocyanate, hexamethylene diisocyanate, the diisocyanate of Jeffamine® D-400, and the like, and mixtures thereof.

The ammonium salt of the carbamate anion is prepared in solution in the presence of an organic, nitrogenous base. The reaction between the primary amine and carbon dioxide to form the ammonium carbamate salt may be represented by the equation (1). The resulting ammonium carbamate salt solutions are normally homogeneous.

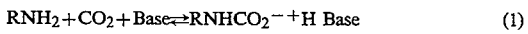 (1)

The result of the reaction of the ammonium carbamate salt with the electrophilic or oxophilic dehydrating agent may be represented by the equation (2).

RNHCO$_2^-$+H Base+"Dehydrating

 (2)

The primary amines for use in the process of the invention are selected from the group consisting of compounds represented by the formula R—NH$_2$, polyoxyalkylene diamines represented by the formula:

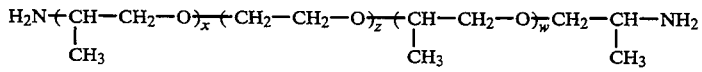

and polyoxyalkylene triamines represented by the formula:

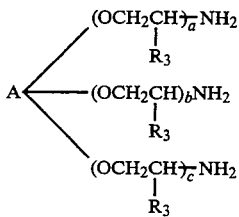

wherein R is selected from the group consisting of linear or branched alkyl, alkenyl, cycloalkyl, cycloalkenyl, aryl, aralkyl, aralkenyl, alkenaryl and alkaryl radicals having 1 to about 22 carbon atoms, a radical represented by the formula:

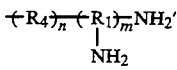

and a radical represented by the formula:

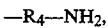

wherein $R_1$, $R_3$, $R_4$, a, b, c, m, n, w, x, z and A are as defined above. Suitable primary amines include diamines and polyamines. In addition, R may contain nonnucleophilic functional groups which do not react preferentially with the electrophilic or oxophilic dehydrating agent. Examples of suitable functional groups include esters, amides, urethanes, carbonates, and the like, and salts thereof.

Examples of primary amines which can be employed in the process of the invention include cyclohexyl amine, octyl amine, 1,4-diaminocyclohexane, aniline, methyl amine, ethyl amine, n-propyl amine, isopropyl amine, n-butyl amine, isobutyl amine, t-butyl amine, n-pentyl amine, isopentyl amine, n-hexyl amine, n-octyl amine, benzyl amine, phenylalanine methyl ester hydrochloride salt, glycine benzyl ester p-toluene sulphonic acid salt, alanine benzyl ester hydrochloride salt, phenyl alanine ethyl ester hydrochloride salt, leucine ethyl ester hydrochloride salt, valine ethyl ester hydrochloride salt, β-alanine ethyl ester hydrochloride salt, glutamic acid ethyl ester hydrochloride salt, 2,6-methylcyclohexyldiamine, 2,4-methylcyclohexyldiamine, n-hexyldiamine, 4,4'-methylene diphenyl amine, hexamethylene diamine, polyoxyalkylenediamines such as those available from Texaco Chemical Company under the trademark Jeffamine ® including D-230 (approximate molecular weight=230), D-400 (approximate molecular weight=400), D-2000 (approximate molecular weight=2,000), D-4000 (approximate molecular weight=4,000), ED-600 (approximate molecular weight=600), ED-900 (approximate molecular weight=900), ED-2001 (approximate molecular weight=2,000), ED-4000 (approximate molecular weight=4,000) and ED-6000 (approximate molecular weight=6,000), polyoxyalkylene triamines such as those available from Texaco Chemical Company under the trademark Jeffamine ® including T-403 (approximate molecular weight=440), T-3000 (approximate molecular weight=3,000) and T-5000 (approximate molecular weight=5,000), tetraethylene pentamine, diethylene triamine, triethylene tetramine, pentaethylene hexamine, and the like, and mixtures thereof.

Applicable solvents for use in the process of the invention are aprotic organic solvents. Both polar and non-polar aprotic organic solvents, as well as mixtures thereof, may be used in the process of the invention. As utilized herein, the phrase "polar aprotic organic solvent" means an aprotic organic solvent having a dielectric constant measured at 25° C. of greater than about 10ε as reported in Reichardt, C., Solvents and solvent effects in organic chemistry, 2nd ed., VCH Verlagsgesellschaft, Weinheim, (1988), Table A-1, utilizing toluene (2.38ε) and tetrahydrofuran (7.58ε) as standards measured at 25° C. Other methods for determining dielectric constants are known and suitable polar aprotic organic solvents are those having a dielectric constant greater than that of tetrahydrofuran utilizing any of such methods.

Examples of non-polar aprotic organic solvents which can be employed in the process of the invention include dichloromethane, toluene, tetrahydrofuran, o-dichlorobenzene, triethylamine and the like, and mixtures thereof. Currently preferred non-polar aprotic organic solvents include dichloromethane and toluene.

Examples of polar aprotic organic solvents which can be employed in the process of the invention include dimethyl formamide, N-methyl-2-pyrrolidone, N,N-dimethyl acetamide, dimethyl sulfoxide, acetonitrile, sulfolane, pyridine and the like, and mixtures thereof. Currently preferred polar aprotic organic solvents include acetonitrile and N,N-dimethyl acetamide.

Although not specifically required, it is preferred to utilize the same solvent to carry out both reaction steps of the present invention in order to avoid additional process equipment for recovering additional solvents.

The amount of solvent utilized in the process of the invention is preferably at least the amount necessary to solubilize the ammonium carbamate salt present.

To obtain high selectivities and yields for the desired isocyanates, a phosphazene compound, an organic, nitrogenous base or mixtures thereof is employed as the base in the process of the invention. The phrase "organic, nitrogenous base" as used herein refers to a base other than the phosphazene compound which is utilized in addition to the reactant primary amine. Applicable organic, nitrogenous bases for use in the process of the invention include guanidine compounds, amidine compounds, tertiary amines, pyridine and mixtures of any two or more thereof.

The phosphazene compounds of the invention are compounds represented by the formula:

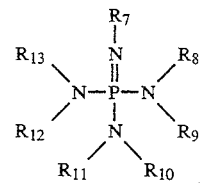

wherein $R_7$, $R_8$, $R_9$, $R_{10}$, $R_{11}$, $R_{12}$ and $R_{13}$ are independently selected from the group consisting of alkyl, aryl, alkaryl, aralkyl and cycloalkyl radicals having 1 to about 22 carbon atoms; or one of $R_8$ or $R_9$ together with one of $R_{10}$ or $R_{11}$, one of $R_{12}$ or $R_{13}$ together with one of $R_{10}$ or $R_{11}$, and $R_7$ together with one of $R_8$ or $R_9$ or one of $R_{12}$ or $R_{13}$ independently form a nitrogen-containing heterocycle; or $R_8$ together with $R_9$, $R_{10}$ together with $R_{11}$, and $R_{12}$ together with $R_{13}$ independently represent a radical represented by the formula:

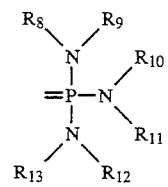

wherein $R_8$, $R_9$, $R_{10}$, $R_{11}$, $R_{12}$ and $R_{13}$ are as defined above.

Examples of phosphazene compounds which can be employed in the process of the invention include, but are not limited to, t-butyliminotris(dimethylamino)-phosphorane ($P_1$-tBu), 1-t-butyl-4,4,4-tris(dimethylamino)-2,2-bis-[tris(dimethylamino) phosphoranylideneamino]-2λ,4λ-catenadi (phosphazene)($P_4$-tBu), 2-t-butylimino-2-diethylamino-1,3-dimethylperhydro-1,3,2-diazaphosphorane (BEMP), t-butyliminotris (diethylamino) phosphorane, 2-t-octylimino-2-diethylamino-1,3-dimethyl-perhydro-1,3,2-diazaphosphorane, and the like, and mixtures of any two or more thereof.

The guanidine compounds of the invention are compounds represented by the formula:

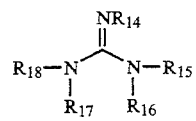

wherein $R_{14}$, $R_{15}$, $R_{16}$, $R_{17}$ and $R_{18}$ are independently selected from the group consisting of alkyl, aryl, alkaryl, aralkyl and cycloalkyl radicals having 1 to about 22 carbon atoms; or $R_{14}$ together with one of $R_{15}$, $R_{16}$, $R_{17}$ or $R_{18}$, $R_{15}$ and $R_{16}$, and $R_{17}$ and $R_{18}$ independently form a nitrogen-containing heterocycle.

The amidine compounds of the invention are compounds represented by the formula:

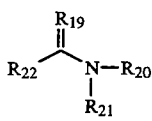

wherein $R_{19}$, $R_{20}$, $R_{21}$ and $R_{22}$ are independently selected from the group consisting of alkyl, aryl, alkaryl, aralkyl and cycloalkyl radicals having 1 to about 22 carbon atoms; or $R_{19}$ together with $R_{20}$ or $R_{21}$ and $R_{22}$ together with $R_{20}$ or $R_{21}$ independently form a nitrogen-containing heterocycle.

Examples of organic, nitrogenous bases which can be employed in the process of the invention include triethylamine, diethyl isopropylamine, trimethylamine, pyridine, tetramethyl guanidine (TMG), cyclohexyl-tetramethyl guanidine (CyTMG), butyltetraethyl guanidine (n-BTEG), cyclohexyl-tetraethyl guanidine (CyTEG), tetraethyl guanidine (TEG), t-butyl-tetraethyl guanidine (t-BTEG), 7-methyl-1,5,7-triazabicyclo[4.4.0]dec-5-ene (MTBD), t-butyl-dimethyl formamidine (t-BDMF), t-butyldimethyl acetamidine (t-BDMA), 1,5-diazabicyclo[4.3.0]non-5-ene (DBN), 1,8-diazabicyclo[5.4.0]undec-7-ene (DBU) and the like, and mixtures of any two or more thereof.

The amount of base, i.e., phosphazene compound, organic, nitrogenous base or mixture thereof, utilized in the process of the invention will depend upon the particular embodiment of the process.

In the first embodiment wherein the ammonium carbamate salt is not recovered prior to reaction with the electrophilic or oxophilic dehydrating agent, the amount of base can be conveniently expressed in terms of a ratio based on the number of equivalents of amine in the primary amine charged. Broadly, the ratio of the number of moles of base to the number of equivalents of amine in the primary amine will be about 1:1 to about 20:1, preferably about 2:1 to about 10:1, and most preferably about 2:1 to about 4:1. The base can be completely charged at the beginning of the process, or a portion may be charged at the beginning of the process and the remainder charged at any time prior to the reaction of the ammonium carbamate salt with the electrophilic or oxophilic dehydrating agent.

In the second embodiment wherein the ammonium carbamate salt is recovered prior to reaction with the electrophilic or oxophilic dehydrating agent, the amount of base can be conveniently expressed in terms of a ratio based on the number of equivalents of amine in the primary amine charged for the reaction of the primary amine with carbon dioxide, and the amount of base can be conveniently expressed in terms of a ratio based on the number of equivalents of carbamate in the ammonium carbamate salt charged for the reaction of the ammonium carbamate salt with the electrophilic or oxophilic dehydrating agent. For the reaction of the primary amine with carbon dioxide, the ratio of the number of moles of base to the number of equivalents of amine in the primary amine will broadly be about 0.5:1 to about 10:1, preferably about 1:1 to about 5:1, and most preferably about 1:1 to about 2:1. For the reaction of the ammonium carbamate salt with the electrophilic or oxophilic dehydrating agent, the ratio of the number of moles of base to the number of equivalents of carbamate in the ammonium carbamate salt will broadly be about 0.5:1 to about 10:1, preferably about 1:1 to about 5:1, and most preferably about 1:1 to about 2:1.

Applicable electrophilic or oxophilic dehydrating agents for use in the process of the invention include anhydrides having the formulas:

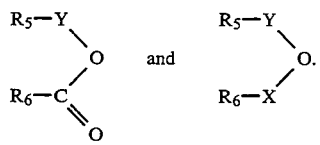

thioanhydrides having the formula:

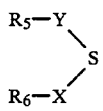

and mixtures thereof wherein X and Y are independently selected from the group consisting of

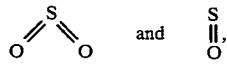

and $R_5$ $R_6$ are independently selected from the group consisting of fluoroalkyl, alkyl, aryl, alkaryl and aralkyl radicals having 1 to about 22 carbon atoms, or $R_5$ and $R_6$ together form a cyclic anhydride or cyclic thioanhydride containing a fused aromatic or cycloaliphatic ring. When $R_5$ and $R_6$ form a fused ring, the preferred aromatic rings are phenyl and naphthyl and the preferred cycloaliphatic rings have about 5 to about 8 carbon atoms.

The fused aromatic or cycloaliphatic ring of the cyclic anhydride or cyclic thioanhydride can be substituted or unsubstituted. Examples of substituents include, but are not limited to, alkyl, halogen, $-NO_2$, and the like, and combinations thereof. Halogen, as used herein, is selected from the group consisting of fluorine, chlorine, bromine and iodine, preferably fluorine and chlorine.

Examples of suitable electrophilic or oxophilic dehydrating agents include 2-sulfobenzoic anhydride, benzenesulfonic anhydride, benzenesulfinic methanesulfonic anhydride, ethanesulfonic methanesulfonic thioanhydride, 2-sulfobenzoic thioanhydride, 2-sulfocyclohexanoic anhydride, cyclohexanecarboxylic ethanesulfonic anhydride, benzenesulfonic thioanhydride, 2-sulfonaphthoic anhydride, 2-sulfocyclooctanoic anhydride, and the like, and mixtures thereof. The currently preferred electrophilic or oxophilic dehydrating agent is 2-sulfobenzoic anhydride because of the high yields achievable with this compound under mild reaction conditions.

In the first embodiment wherein the ammonium carbamate salt is not recovered prior to reaction with the electrophilic or oxophilic dehydrating agent, the amount of electrophilic or oxophilic dehydrating agent can be conveniently expressed in terms of a ratio based on the number of equivalents of amine in the primary amine charged. Broadly, the ratio of the number of moles of electrophilic or oxophilic dehydrating agent to the number of equivalents of amine in the primary amine will be about 0.4:1 to about 10:1, preferably about 0.9:1 to about 5:1 and most preferably about 1:1 to about 2:1.

In the second embodiment wherein the ammonium carbamate salt is recovered prior to reaction with the electrophilic or oxophilic dehydrating agent, the amount of electrophilic or oxophilic dehydrating agent can be conveniently expressed in terms of a ratio based on the number of equivalents of carbamate in the ammonium carbamate salt charged for the reaction of the ammonium carbamate salt with the electrophilic or oxophilic dehydrating agent. Broadly, the ratio of the number of moles of electrophilic or oxophilic dehydrating agent to the number of equivalents of carbamate in the ammonium carbamate salt will be about 0.4:1 to about 10:1, preferably about 0.9:1 to about 5:1, and most preferably about 1:1 to about 2:1.

The reaction between the primary amine and carbon dioxide is conducted under a $CO_2$ atmosphere. The pressure of $CO_2$ during this reaction is 0 psig (atmospheric pressure) to about 150 psig, preferably 0 psig to about 100 psig, and most preferably 0 psig to about 80 psig. It is preferred to charge the $CO_2$ to the reaction vessel containing the primary amine below the liquid level in the reaction vessel. Although not specifically required, it is preferred to conduct the reaction of ammonium carbamate salt with electrophilic or oxophilic dehydrating agent under a $CO_2$ atmosphere. However, the reaction of ammonium carbamate salt with electrophilic or oxophilic dehydrating agent can be conducted under any inert atmosphere, e.g. nitrogen, argon or air, provided the atmosphere is substantially dry. A substantially dry atmosphere is critical because water will react with the electrophilic or oxophilic dehydrating agent. The pressure during this reaction is 0 psig to about 150 psig, preferably 0 psig to about 100 psig, and most preferably 0 psig to about 80 psig.

The temperature and time used in the process of the invention will depend on the particular reaction involved. For the reaction of primary amine with $CO_2$, the temperature is about $-78°$ C. to about $100°$ C., preferably about $10°$ C. to about $40°$ C., and most preferably about $20°$ C. to about $30°$ C. The time will broadly be the time required to achieve complete mixing of reactants to about 4 hours, preferably about 5 minutes to about 1 hour, and most preferably about 10 minutes to about 30 minutes. For the reaction of ammonium carbamate salt with electrophilic or oxophilic dehydrating agent, the temperature is about $-78°$ C. to about $100°$ C., preferably about $-20°$ C. to about $30°$ C., and most preferably about $-10°$ C. to about $10°$ C. The time will broadly be the time required to achieve complete mixing of the reactants to about 4 hours, preferably about 1 minute to about 30 minutes, and most preferably about 5 minutes to about 10 minutes.

For the embodiment where the ammonium carbamate salt is recovered prior to reaction with the electrophilic or oxophilic dehydrating agent, the ammonium carbamate salt can be recovered by any conventional means known in the art.

The desired isocyanates produced by the process of the invention can be recovered by any conventional means known in the art, such as that disclosed in the examples herein.

Contemplated equivalence of the general formulas set forth above for the primary amines, isocyanates and electrophilic or oxophilic dehydrating agents are compounds otherwise corresponding thereto and having the same general properties wherein one or more of the various R groups are simple variations of the substituents as defined therein.

In addition, where a substituent is designated as, or can be, a hydrogen, the exact chemical nature of a substituent which is other than hydrogen at that position is not critical so long as it does not adversely effect the overall synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The invention will now be further disclosed in the following illustrative examples wherein parts and percentages are given on a molar basis unless otherwise specified.

EXAMPLES

All amines used in the following examples were obtained either from Aldrich Chemical Company or Kodak Chemical Company and were used as received. Acetonitrile, toluene, methylene chloride and triethylamine were purchased from Aldrich Chemical Company. 2-Sulfobenzoic anhydride was obtained from Fluke Chemical Corp CyTEG (N-cyclohexyl-N', N', N'', N''-tetraethyl guanidine) was synthesized according to the general procedure set forth in Bredereck, H. and Bredereck, K., Chem. Ber., 94, 2278–2295(1961). Carbon dioxide was supplied either from Matheson (bone dry grade) or from Acetylene Gas Company (welding grade) and used without any further purification.

Gas chromatographic analysis was performed on a Varian model 3400 gas chromatograph with a model 8000 auto sampler using a 30 meter Megabore DB-1 (3 µm) J&W Scientific column.

EXAMPLE 1 n-Octyl isocyanate:

A Fischer-Porter bottle was charged with 1.29g (10 mmol) n-octyl amine, 3 g (30 mmol) triethylamine, 154mg (1 mmol) biphenyl as G. C. internal standard and 20 mL $CH_3CN$. At room temperature, 80 psig carbon dioxide was added above this solution (white ppt. formed upon $CO_2$ addition which went homogeneous within 5 min). After 1 h this solution was cooled to ca. 0° C. A second Fischer-Porter bottle was charged with 2.7 g (15 mmol) 2-sulfobenzoic anhydride (obtained from Fluka and used as received) and 20 mL $CH_3CN$ (homogeneous solution). After 1 h this solution was also cooled to 0° C. The carbamate solution generated in the first Fischer-Porter bottle was added all at once to the sulfobenzoic anhydride solution under 80 psig $CO_2$ giving an exothermic reaction (solution warmed from 0° C to 11° C.). Aliquots were taken periodically and each diluted with diethyl ether and analyzed by G.C. G.C. yield of n-octyl isocyanate after 5 min was calculated to be 94% (Run 1).

Additional runs (Runs 2-6) were made according to the above procedure varying the type and amount of base, solvent and the amount of 2-sulfobenzoic anhydride. The results of all runs can be found in Table I.

TABLE I

Reaction of n-Octyl Amine Carbamate with 2-Sulfobenzoic Anhydride[1]

| Run No. | Base, mmol CyTEG | Base, mmol Et₃N | Solvent | 2-sulfobenzoic Anhydride (mmol) | % Yield n-Octyl-NCO |
|---|---|---|---|---|---|
| 1 | 0 | 30 | CH₃CN | 15 | 94 |
| 2 | 0 | 20 | CH₃CN | 15 | 82.5 |
| 3 | 0 | 40 | CH₃CN | 15 | 77.5 |
| 4 | 11 | 20 | CH₂Cl₂ | 10 | 62 |
| 5 | 11 | 20 | CH₂Cl₂ | 15 | 87.5 |
| 6 | 11 | 20 | toluene | 15 | 67 |

[1]All reactions were run with 10 mmol n-octyl amine under 80 psig CO₂ at ca. 0° C. All reactions were exothermic and yields of n-octyl isocyanate were determined by gas chromatographic analysis using biphenyl as an internal standard. Reaction time to maximum yield was 5-60 min in all runs except Run 6 (reaction in toluene as solvent) which was 3.5 hr.

That which is claimed is:

1. A process for preparing an isocyanate comprising:
   (a) contacting $CO_2$ and a primary amine in the presence of an aprotic organic solvent and a base selected from the group consisting of a phosphazene compound, an organic, nitrogenous base and mixtures thereof, wherein said organic, nitrogenous base is selected from the group consisting of guanidine compounds, amidine compounds, tertiary amines, pyridine and mixtures thereof, under reaction conditions of time and temperature sufficient to produce the corresponding ammonium carbamate salt, and
   (b) reacting said ammonium carbamate salt with an electrophilic or oxophilic dehydrating agent selected from the group consisting of anhydrides having the formulas:

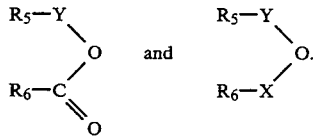

thioanhydrides having the formula:

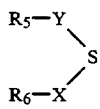

and mixtures thereof wherein X and Y are independently selected from the group consisting of

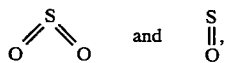

$R_5$ and $R_6$ are independently selected from the group consisting of alkyl, fluoroalkyl, aryl, alkaryl and aralkyl radicals having 1 to about 22 carbon atoms, or $R_5$ and $R_6$ together form a cyclic anhydride or cyclic thioanhydride containing a fused aromatic or cycloaliphatic ring at a temperature of $-78°$ C. to $100°$ C. and a time sufficient to produce the corresponding isocyanate.

2. The process according to claim 1 wherein said aprotic organic solvent is selected from the group consisting of dichloromethane, tetrahydrofuran, acetonitrile, o-dichlorobenzene, toluene, N,N-dimethylacetamide and pyridine.

3. The process according to claim 2 wherein said aprotic organic solvent is present in at least an amount sufficient to solubilize said ammonium carbamate salt.

4. The process according to claim 1 wherein the ratio of the number of moles of said base to the number of equivalents of amine in said primary amine starting material is 1:1 to about 20:1.

5. The process according to claim 4 wherein the ratio of the number of moles of said base to the number of equivalents of amine in said primary amine starting material is about 2:1 to about 10:1.

6. The process according to claim 1 wherein the ratio of the number of moles of said electrophilic or oxophilic dehydrating agent to the number of equivalents of amine in said primary amine starting material is about 0.4:1 to about 10:1.

7. The process according to claim 1 wherein said primary amine is selected from the group consisting of compounds represented by the formula $R-NH_2$, polyoxyalkylene diamines represented by the formula:

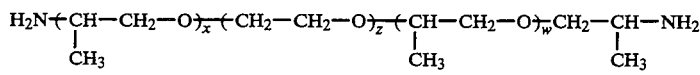

and polyoxyalkylene triamines represented by the formula:

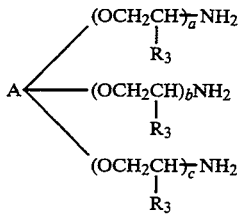

wherein R is selected from the group consisting of alkyl, alkenyl, cycloalkyl, cycloalkenyl, aryl, aralkyl, aralkenyl, alkenaryl and alkaryl radicals having 1 to about 22 carbon atoms, a radical represented by the formula:

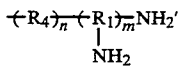

and a radical represented by the formula $-R_4-NH_2$, or R as defined above containing nonnucleophilic functional groups; wherein $R_1$ and $R_4$ are independently selected from the group consisting of alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, $x+w$ represents an integer from about 2 to about 70, z represents an integer from 0 to about 90, $x+w+z$ represents an integer from about 2 to about 100, a, b and c independently represent an integer from about 2 to about 30, and A represents a trihydric alcohol initiator.

8. The process according to claim 7 wherein said nonnucleophilic functional groups are selected from the group consisting of esters, amides, urethanes, carbonates and salts thereof.

9. A process according to claim 1 wherein said isocyanate is represented by the formula:

$$R_2-N=C=O$$

wherein $R_2$ is selected from the group consisting of alkyl, alkenyl, cycloalkyl, cycloalkenyl, aryl, aralkyl, aralkenyl, alkenaryl and alkaryl radicals having 1 to about 22 carbon atoms, a radical represented by the formula:

$$\mathrm{+R_4)_n\!+\!R_1)_m\!N\!=\!C\!=\!O} \atop \mathrm{N\!=\!C\!=\!O}$$

a radical represented by the formula:

$$-R_4-N=C=O,$$

a radical represented by the formula:

$$\mathrm{+CH-CH_2-O)_x\!+\!CH_2-CH_2-O)_z\!+\!CH-CH_2-O)_w\!CH_2-CH-N=C=O} \atop \mathrm{CH_3 \qquad\qquad\qquad\qquad CH_3 \qquad\qquad CH_3}$$

or $R_2$ as defined above containing nonnucleophilic functional groups; or said isocyanate is represented by the formula:

$$A\!\!\bigg\langle\!\!\begin{array}{l}(OCH_2CH)_a\!N\!=\!C\!=\!O\\ \quad|\\ \quad R_3\\ (OCH_2CH)_b\!N\!=\!C\!=\!O\\ \quad|\\ \quad R_3\\ (OCH_2CH)_c\!N\!=\!C\!=\!O\\ \quad|\\ \quad R_3\end{array}$$

wherein $R_1$ and $R_4$ are independently selected from the group consisting of alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, $R_3$ is hydrogen or methyl, x+w represents an integer from about 2 to about 10, z represents an integer from 0 to about 90, x+w+z represents an integer from about 2 to about 100, a, b and c independently represent an integer from about 2 to about 30, and A represents a trihydric alcohol initiator.

10. The process according to claim 9 wherein said nonnucleophilic functional groups are selected from the group consisting of esters, amides, urethanes, carbonates and salts thereof.

11. The process according to claim 1 wherein said electrophilic or oxophilic dehydrating agent is 2sulfobenzoic anhydride.

12. The process according to claim 1 wherein said temperature of (b) is about −20° C. to about 30° C.

13. A process for preparing an isocyanate comprising:
(a) contacting $CO_2$ and a primary amine in the presence of an aprotic organic solvent and a base selected from the group consisting of a phosphazene compound, an organic, nitrogenous base and mixtures thereof wherein said organic, nitrogenous base is selected from the group consisting of guanidine compounds, amidine compounds, tertiary amines, pyridine and mixtures thereof, under reaction conditions of time and temperature sufficient to produce the corresponding ammonium carbamate salt,
(b) recovering said ammonium carbamate salt, and
(c) reacting said ammonium carbamate salt with an electrophilic or oxophilic dehydrating agent selected from the group consisting of anhydrides having the formulas:

$$\begin{array}{cc}\mathrm{R_5-Y}\!\!\!\diagdown & \mathrm{R_5-Y}\!\!\!\diagdown\\ \quad\;\;\diagdown\!\mathrm{O} \quad\mathrm{and} & \quad\;\;\diagdown\!\mathrm{O}.\\ \mathrm{R_6-C}\!\!\!\diagup & \mathrm{R_6-X}\!\!\!\diagup\\ \quad\;\;\|\\ \quad\;\;\mathrm{O}\end{array}$$

thioanhydrides having the formula:

$$\begin{array}{c}\mathrm{R_5-Y}\!\!\!\diagdown\\ \quad\;\;\diagdown\!\mathrm{S}\\ \mathrm{R_6-X}\!\!\!\diagup\end{array}$$

and mixtures thereof wherein X and Y are independently selected from the group consisting of $$\begin{array}{cc}\mathrm{S}\\ \diagup\!\!\diagdown & \mathrm{S}\\ \mathrm{O} \quad\;\mathrm{O} \quad\mathrm{and} & \|,\\ & \mathrm{O}\end{array}$$

$R_5$ and $R_6$ are independently selected from the group consisting of alkyl, fluoroalkyl, aryl, alkaryl and aralkyl radicals having 1 to about 22 carbon atoms, or $R_5$ and $R_6$ together form a cyclic thioanhydride containing a fused aromatic or cycloaliphatic ring in the presence of an aprotic organic solvent and a base selected from the group consisting of a phosphazene compound, an organic, nitrogenous base and mixtures thereof, wherein said organic, nitrogenous base is selected from the group consisting of guanidine compounds, amidine compounds, tertiary amines, pyridine and mixtures thereof, at a temperature of −78° C. to 100° C. and a time sufficient to produce the corresponding isocyanate.

14. The process according to claim 13 wherein said aprotic organic solvent is selected from the group consisting of dichloromethane, tetrahydrofuran, acetonitrile, o-dichlorobenzene, toluene, N,N-dimethylacetamide and pyridine.

15. The process according to claim 14 wherein said aprotic organic solvent is present in at least an amount sufficient to solubilize said ammonium carbamate salt.

16. The process according to claim 13 wherein the ratio of the number of moles of said base to the number of equivalents of amine in said primary amine starting material in step (a) is 0.5:1 to about 10:1, and the ratio of the number of moles of said base to the number of equivalents of carbamate in said ammonium carbamate salt starting material in step (c) is 0.5:1 to about 10:1.

17. The process according to claim 16 wherein the ratio of the number of moles of said base to the number of equivalents of amine in said primary amine starting material in step (a) is 1:1 to about 5:1, and the ratio of the number of moles of said base to the number of equivalents of carbamate in said ammonium carbamate salt starting material in step (c) is 1:1 to about 5:1.

18. The process according to claim 13 wherein the ratio of the number of moles of said electrophilic or oxophilic dehydrating agent to the number of equivalents of carbamate in said ammonium carbamate salt starting material in step (c) is about 0.4:1 to about 10:1.

19. The process according to claim 13 wherein said primary amine is selected from the group consisting of compounds represented by the formula R—NH$_2$, polyoxyalkylene diamines represented by the formula:

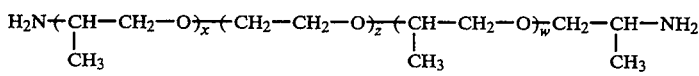

and polyoxyalkylene triamines represented by the formula:

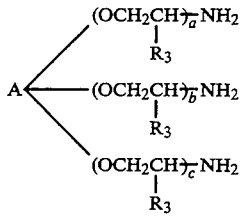

wherein R is selected from the group consisting of alkyl, alkenyl, cycloalkyl, cycloalkenyl, aryl, aralkyl, aralkenyl, alkenaryl and alkaryl radials having 1 to about 22 carbon atoms, a radial represented by the formula:

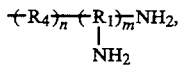

and a radical represented by the formula —R$_4$—NH$_2$, or R as defined above containing nonnucleophilic functional groups; wherein R$_1$ and R$_4$ are independently selected from the group consisting of alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, R$_3$ is hydrogen or methyl, x+w represents an integer from about 2 to about 70, z represents an integer from 0 to about 90, x+w+z represents an integer from about 2 to about 100, a, b and c independently represent an integer from about 2 to about 30, and A represents a trihydric alcohol initiator.

20. The process according to claim 19 wherein said nonnucleophilic functional groups are selected from the group consisting of esters, amides, urethanes, carbonates and salts thereof.

21. A process according to claim 13 wherein said isocyanate is represented by the formula:

wherein R$_2$ is selected from the group consisting of alkyl, alkenyl, cycloalkyl, cycloalkenyl, aryl, aralkyl, aralkenyl, alkenaryl and alkaryl radicals having 1 to about 22 carbon atoms, a radical represented by the formula:

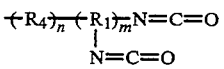

a radical represented by the formula:

a radical represented by the formula:

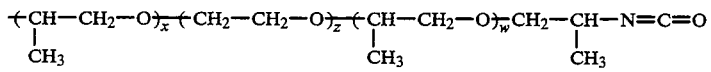

or R$_2$ as defined above containing nonnucleophilic functional groups; or said isocyanate is represented by the formula:

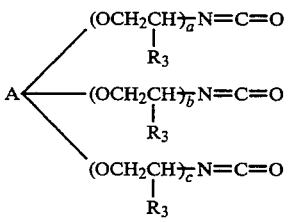

wherein R$_1$ and R$_4$ are independently selected from the group consisting of alkyl, alkenyl, cycloalkyl, cycloalkenyl, aryl, aralkyl, aralkenyl, alkenaryl and alkaryl radicals having 1 to about 22 carbon atoms, m represents an integer from 0 to about 100, n represents an integer from 0 to about 8, R$_3$ is hydrogen or methyl, x+w represents an integer from about 2 to about 70, z represents an integer from 0 to about 90, x+w+z represents an integer from about 2 to about 100, a, b and c independently represent an integer from about 2 to about 30, and A represents a trihydric alcohol initiator.

22. The process according to claim 21 wherein said nonnucleophilic functional groups are selected from the group consisting of esters, amides, urethanes, carbonates and salts thereof.

23. The process according to claim 13 wherein said electrophilic or oxophilic dehydrating agent is 2-sulfobenzoic anhydride.

24. The process according to claim 13 wherein said temperature of (c) is about −20° C. to about 30° C.

* * * * *